United States Patent [19]

Cavitt

[11] 4,321,206

[45] Mar. 23, 1982

[54] ETHYLENE OXIDE PRODUCTION

[75] Inventor: Stanley B. Cavitt, Austin, Tex.

[73] Assignee: Texaco Development Corporation, White Plains, N.Y.

[21] Appl. No.: 53,624

[22] Filed: Jun. 29, 1979

Related U.S. Application Data

[60] Division of Ser. No. 930,961, Aug. 4, 1978, Pat. No. 4,206,128, which is a continuation-in-part of Ser. No. 697,088, Jun. 16, 1976, abandoned.

[51] Int. Cl.$^3$ .......................................... C07D 301/22
[52] U.S. Cl. .................................................. 260/348.34
[58] Field of Search .................................... 260/348.34

[56] References Cited

U.S. PATENT DOCUMENTS

| | | | |
|---|---|---|---|
| 3,702,259 | 11/1972 | Nielsen | 252/463 |
| 3,956,184 | 5/1976 | Kruglikov et al. | 252/463 X |
| 4,007,135 | 2/1977 | Hayden et al. | 260/348.34 X |
| 4,012,425 | 3/1977 | Nielsen et al. | 260/348.34 X |

OTHER PUBLICATIONS

Ely Gonick et al., Jour. Am. Chem. Soc., vol. 76 (1954), p. 5253.

G. Schwarzenbach, Helvetica Chimica Acta, vol. 36, No. 6 (1953), pp. 23–36.

M. D. Joesten et al., Jour. Inorg. Nucl. Chem. (1967), vol. 29, pp. 1421–1436.

*Primary Examiner*—Norma S. Milestone
*Attorney, Agent, or Firm*—Carl G. Ries; Thomas H. Whaley; Walter D. Hunter

[57] ABSTRACT

An improved method is disclosed for the vapor phase epoxidation of ethylene to ethylene oxide which includes intimately contacting an ethylene-containing feed stream with an epoxidizing amount of molecular oxgyen epoxidizing agent in the presence of a catalytically effective amount of a novel supported, activated silver catalyst and, preferably in the presence of an effective amount of at least one inhibitor which retards combustion of ethylene to carbon dioxide at a temperature of from about 200° C. to about 300° C.

The novel silver catalyst is best described in terms of its method of preparation. The catalyst is prepared by impregnating certain inorganic porous substrates with a specific silver carboxylate/amine complex impregnating solution. The impregnated support it then heated in order to evaporate volatiles, decompose the complex and activate the catalyst.

8 Claims, No Drawings

ETHYLENE OXIDE PRODUCTION

This is a division, of application Ser. No. 930,961, filed Aug. 4, 1978, now U.S. Pat. No. 4,206,128, which in turn is a continuation-in-part of Ser. No. 697,088, filed June 16, 1976, abandoned.

BACKGROUND OF THE INVENTION

1. Field of the Invention

This invention relates to vapor phase epoxidation reactions of ethylene with molecular oxygen; and, more particularly to epoxidation reactions using specific activated silver catalyst.

2. Description of Prior Art

The preparation of ethylene oxide by the oxidation of ethylene in the presence of suitable catalysts is well known. These known processes can be generally separated into two groups; the first utilizes air and the second utilizes molecular oxygen, e.g., from about 85 mol percent to about 99 mol percent. "Silver catalysts" are utilized with both groups.

Although the first references to the use of silver as such a catalyst was made by Walter in British Pat. No. 21,941 (1905), it was not until some thirty years later that the first disclosures were made of the use of silver as a catalyst in the vapor phase oxidation of ethylene to ethylene oxide. See Societe Francaise de Catalyse Generalisee, French Pat. No. 729,952 (1932); and Lefort, U.S. Pat. No. 1,998,878 (1935).

Since silver is expensive, optimizing the amount of silver employed in a supported catalyst for a desired conversion and selectivity to products has been widely investigated. A variety of techniques have been developed fro the depositing of relatively small, but highly active amounts of silver on surfaces of non-silver supports such as alumina. For example, McKim and Cambron in *Canadian Journal of Research*, Volume 27, Section B (1949), pp. 813–827, describe a method for depositing particulate silver on a support by decomposing silver oxalate in aqueous ethanolamine at 60° C. and forming a paste which is applied to the surface of the support. In U.S. Pat. No. 3,043,854 issued July 10, 1962, to Endler, a silver coating formed by decomposition of a silver carbonate slurry is applied to a catalyst support surface.

Recently it has been disclosed that supported silver catalysts can be prepared by impregnating a porous substrate with certain silver containing solutions and evaporating or decomposing the solutions to deposit silver on the substrate. U.S. Pat. No. 3,702,259 to Nielsen describes the use of an aqueous silver oxalate impregnating solution which employs a solubilizing/reducing agent of ethylenediamine, a mixture of ethylenediamine or ethanolamine and ammonia, or a mixture of ethylenediamine and ethanolamine. Van Bylandtlaan, in Belgium Pat. No. 808,278 (1974) employs an aqueous solution of hexamethylenetetramine with an ethylenediamine silver complex to deposit silver on an alumina support by decomposition. Additionally, it has been disclosed in Japanese Pat. No. 71/19,606 to Fujii et al that impregnation of inorganic supports with aqueous silver nitrate/alkanolamine complexes with subsequent thermal decomposition gives supported silver catalysts for ethylene epoxidation.

It has now been discovered that an extremely stable, physically durable, supported silver catalyst used in accordance with commercially known processes such as described in U.S. Pat. No. 3,119,837, British Pat. Nos. 1,314,613 and 1,132,095, results in a process which gives higher unit productivity and selectivity to the desired product at lower operating temperatures. The selectivity is particularly important in air processes which are not closed systems because some proportion of the unreacted ethylene is lost by venting excess gas. The catalyst utilized in the inventive process can be simply produced by impregnating certain types of porous, inorganic substrates with a complex formed by dissolving a silver carboxylate in certains amines and thermally decomposing the complex to deposit the silver on the substrate and activate the silver. Additionally, the catalysts used in accordance with the instant process show high attrition resistance and surprisingly high mechanical strength.

SUMMARY OF THE INVENTION

According to the broad aspect of the invention, ethylene is epoxidized to ethylene oxide substantially in the vapor phase by intimately contacting ethylene with an epoxidizing amount of molecular oxygen in the presence of a catalytically effective amount of an activated silver containing catalyst at temperatures of from about 200° C. to about 300° C. Preferably, the ethylene is contacted with the molecular oxygen in the presence of an effective amount of at least one inhibitor which retards combustion of ethylene to carbon dioxide.

The activated silver containing catalyst is prepared by impregnating certain porous, inorganic substrates with a silver carboxylate/amine complex impregnating solution and heating the impregnated substrate at temperature of from about 50° C. to 300° C. to evaporate volatiles, decompose the complex, and activate the catalyst.

The impregnating solution is formed by dissolving a silver carboxylate in a solubilizing amount of an amine-containing complexing agent selected from:

(a) alicyclic diamines wherein at least one amino moiety is primary or secondary, but no more than one is primary;

(b) polyamines containing at least three amino moieties wherein at least one is primary or secondary; or (c) amino ethers containing at least one ether linkage and at least one amino moiety which is primary or secondary.

DESCRIPTION OF THE PREFERRED EMBODIMENTS

In accordance with a preferred embodiment, ethylene is epoxidized to ethylene oxide in a continuous process by contacting a feed material which comprises from about 5 mol % to about 7 mol % ethylene, from about 5 mol % to about 6 mol % oxygen, from about 6 mol % to about 8 mol % carbon dioxide, trace amounts of a suitable inhibitor and the remainder nitrogen. The feed stream is contacted with a catalytically effective amount of a specific activated, supported silver-containing catalyst, in vapor phase, at temperatures from about 220° C. to about 260° C. and at pressures in the range of from about 13 atm. to about 20 atm.

As more particularly described hereinafter, the supported silver catalyst used in the instant invention process is prepared by impregnating a porous inorganic substrate with a silver carboxylate/amine complex and heating the impregnated substrate at a temperature of from 50° C. to 300° C. to evaporate volatiles, decompose the complex and activate the catalyst.

The Oxidation Reaction

The epoxidation of ethylene to ethylene oxide can best be described as a controlled oxidation. It is important to minimize complete oxidation in accordance with the instant process while maximizing the selectivity and conversion to the desired epoxidized product.

The process parameters used in accordance with the instant invention are generally well known in the art. Particular parameters which can effect the advantageous results obtained by use of the novel activated, silver catalyst material can be determined without undue experimentation by the skilled artisan in light of the teachings herein.

Generally, the process is carried out in a vapor phase process wherein a single gaseous feed stream is continuously charged to a suitable catalyst containing reactor. The catalyst material is contained on a suitable support as hereinafter described.

The reaction is carried out at temperatures from about 200° C. to about 300° C., and preferably in the range of about 220° C. to about 260° C. The pressures are not critical and may vary from about atmospheric to about 35 atm. with about 13 atm. to about 20 atm. being preferred at the preferred temperature range. The feed admixture is preferably fed in a single stream to the reactor in order that the constituents be thoroughly admixed.

The feed admixture contains ethylene, molecular oxygen, diluents and inhibitors. The molecular oxygen employed as an epoxidizing agent in the process can consist essentially of relatively pure oxygen or that molecular oxygen contained in air. A typical concentrated oxygen gas, suitable for use as a make-up oxygen reactant in the process of this invention comprises the concentrated oxygen gas consisting of oxygen, nitrogen and argon from the fractional distillation of air. The molecular oxygen content in this molecular oxygen mixture can range from 85 mol % to higher than 98 mol %, with a preferable mol % being 90 to 97%. The feed admixture contains from about 3 mol % to about 10 mol % oxygen based on the total feed with 5 mol % to about 8 mol % being preferable.

The ratio of oxygen to ethylene in the feed must be of such a value that acceptable conversion is obtained without creating an explosive mixture. It will be realized by the skilled artisan that the exact mixture will depend upon such factors as the amount of inhibitor present, the actual inhibitor used, the amount of diluent present, the diluent or mixtures thereof used, as well as the particular temperature and pressure parameters involved in the reaction.

Although dependent on numerous parameters, generally, the ratio of ethylene to molecular oxygen introduced into the ethylene oxidation system should be controlled such that the molar ratio of ethylene to oxygen in the feed is from about 0.5 to about 10.0 and preferably in the range from about 1.0 to about 3.0.

Generally, the ethylene can be present in amounts from about 2 to about 30 mol % and preferably from about 5 to about 20 mol % based on the total feed composition.

The concentration of the feed constituents may be varied by controlled addition of diluents and/or inhibitors. Diluents which may be present in the feed can be generally described as those gases which are substantially inert to the desired oxidation reaction.

One class of useful diluents includes saturated polyhydrocarbons such as for example ethane, propane and higher saturated hydrocarbons. It will be realized by those skilled in the art that saturated hydrocarbons having generally more than about 3 carbon atoms are not practical for use in accordance with the preferred embodiment of the instant invention. The saturated polyhydrocarbon while being substantially inert to the oxidation reaction, have been shown to effectively promote the catalytic activity.

Carbon dioxide may also be useful as a diluent. The presence of carbon dioxide, however, serves to retard the catalytic activity and thus may likewise serve as an inhibitor. Gases which are totally inert to the reaction can also be utilized. Examples include methane, nitrogen, argon and the like.

The feed may also contain an inhibitor to minimize complete oxidation of the olefin. Any one of a number of commercially available inhibitors can be employed, such as ethylene dichloride, vinyl chloride, dichlorobenzene, monochlorobenzene, dichloromethane, or chlorinated bi-phenyls and chlorinated polyphenyls with ethylene dichloride being preferable.

The amount of inhibitor utilized can be readily determined by known methods. Generally, it can be added in amounts in the range of about 0.01 ppm to about 0.5 ppm for a 7–10% molar ethylene composition feed, with 0.01 to 0.05 ppm being preferable. Amounts up to 3.0 ppm may be needed with ethylene feeds which contain substantial amounts of polyhydrocarbons.

The amount of diluent present can generally be determined by the skilled artisan. When methane is present, amounts up to about 30 mol % of the total reactor feed may be utilized provided that the total hydrocarbon-oxygen ratio is kept outside the explosive limits. Polyhydrocarbons such as ethane, may be present in amounts up to about 30% if sufficient amounts of reaction inhibitors, such as carbon dioxide or ethylene dichloride are present to balance the reaction-promoting effect.

Carbon dioxide can be used in concentrations from trace amounts up to about 50 mol % of the total feed. Amounts from about 2 mol % to 20 mol % are preferred. Preferably carbon dioxide and nitrogen are used as inert diluents for economic and safety reasons.

The flow rates will vary depending on the feed admixture. These rates can be readily determined by the artisan. Generally, mass hourly space velocities (MHSV) of from about 2.5 grams of feed per gram catalyst per hour to about 25 grams of feed per gram catalyst per hour has been found sufficient. An MHSV of 5.0 to 8.0 is preferred.

According to a particularly preferred embodiment a single admixed feed stream comprises from 5 to 7 mol % ethylene; from 5 to 6 % oxygen; 6 to 8 mol % carbon dioxide, 79 to 84 mol % nitrogen; and trace amounts of ethylene dichloride. The stream is continuously fed to one end of a vertical, parallel-tube reactor which is uniformly packed with catalyst material which is spherical in shape. The ethylene oxide contained in the reactor effluent is removed by conventional means such as scrubbers and the like. Gaseous by-products such as carbon dioxide are also removed and the remaining effluent recycled.

The Catalyst

The silver containing catalyst can best be described in terms of its preparation. A porous, inorganic substrate is impregnated with a silver carboxylate/amine complex impregnating solution and heated at temperatures of from 50° C. to 300° C. to evaporate volatiles, decompose the complex, and activate the catalyst.

In accordance with a preferred embodiment, the novel supported silver catalyst of the instant invention is prepared in four steps. In a first step, a silver carboxylate/amine complex, as more fully described hereinafter, is prepared by dissolving a silver carboxylate in an excess of a polyalkylene polyamine having terminal primary nitrogen moieties at temperatures sufficient to dissolve the silver carboxylate.

In a second step, an inorganic porous support, as more fully described hereinafter, and preferably a high-purity α-alumina support, is impregnated by immersing the support in the silver carboxylate/amine complex at about atmospheric pressure and then subjecting the immersed support to vacuum at temperatures of from about 0° C. to about 50° C. and more preferably 20° C. to 40° C. After the vacuum is broken, the excess complex is drained.

In a third step, the drained support is heated to evaporate volatiles at temperatures of from about 50° C. to 150° C. in a forced-air heater for a time from about 1 to about 12 hours. In a final step, the dried, impregnated support is heated in the presence of forced air at temperatures of from about 150° C. to about 300° C. to decompose the silver carboxylate/amine complex and activate the supported silver catalyst material.

The impregnating solution of the instant invention comprises a silver carboxylate/amine complex which may contain a suitable solvent. The impregnating solution can best be characterized as a homogeneous liquid at impregnating temperatures which is formed by solubilizing a silver salt of an organic acid in a solubilizing amount of certain amine-containing complexing agents. Surprisingly, these silver carboxylate/amine complexes are stable in high silver concentrations at impregnating temperatures and contain large amounts of silver which are carried to the support, while simultaneously yielding a solution of a viscosity which is suitable for impregnation of porous, inorganic supports.

The silver carboxylate/amine complex impregnating solutions of the instant invention can best be described in terms of their method of preparation. Specifically, a silver salt of an organic acid is dissolved in a solubilizing amount of certain amine-containing complexing agents at temperatures in the range of from about 0° to about 50° C.

The useful silver salts of organic acids can be generally described as silver carboxylates which readily thermally decompose. Such compounds can be carboxylates of mono-carboxylic or poly-carboxylic acids. Preferably, the silver salt is of a mono-carboxylic or di-carboxylic acid, wherein the organic moiety contains less than about 10 carbon atoms. Those carboxylates of less than about 20 carbon atoms are preferred in order to obtain a favorable concentration of silver in the organic acid salt, and ultimately thus in the complex solution, while providing for facile thermal decomposition. It should be noted that while silver salts of organic acids containing more than about 10 carbon atoms are useful, they produce a silver amine complex which becomes increasingly difficult to decompose as the molecular weight increase and will reduce the amount of silver ultimately deposited on the support.

Examples of suitable silver carboxylates include silver carbonate, silver acetate, silver malonate, silver glycolate, silver oxalate, silver formate, silver citrate, silver lactate, silver pyruvate, and the like. The most preferred silver carboxylates are silver oxalate and silver acetate because of availability and solubility.

The useful amine containing complexing agents of the instant invention can be generically described as:

(a) alicyclic diamines wherein at least one amino moiety is primary or secondary provided no more than one amino moiety is primary;

(b) polyamines containing at least three amino moieties wherein at least one is primary or secondary; and (c) amino ethers containing at least one ether (oxy) linkage wherein at least one amino moiety is primary or secondary.

Although all alicyclic diamines meeting the above criteria are useful as complexing agents, a preferred group of such diamines comprises piperazines, the N-alkyl substituted piperazines and the C alkyl substituted piperazines.

While all aliphatic polyamines containing at least three amino moieties wherein at least one is primary are useful as complexing agents, a preferred group is the polyalkylene polyamines of the formula

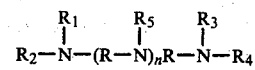

wherein R is a straight or branched chain alkylene radical having from 2 to about 4 carbon atoms, $R_1$, $R_2$ $R_3$, $R_4$ and $R_5$ are, independently, hydrogen or an alkyl radical of from 1 to 5 carbon atoms provided at least one of $R_1$, $R_2$, $R_3$, $R_4$ or $R_5$ is hydrogen; or $R_1$ and $R_2$ or $R_3$ and $R_4$ with the nitrogen to which they are attached form a piperazine ring and n is an integer of from 1 to about 4. Examples include N(aminoethyl)-piperazine, N,N'-bis(2-aminoethyl)piperazine, diethylenetriamine, N-methyldiethylenetriamine, triethylenetetramine and the like. The most preferred polyalkylene polyamine compounds are diethylenetriamine and triethylenetetramine.

The amino ethers that are useful within the scope of the instant invention are the saturated and unsaturated, substituted and unsubstituted aliphatic amino ethers. These compounds may be straight or branched chain, acrylic, alicyclic, heterocyclic or cyclic. Examples of such compounds include morpholine, the C-substituted morpholines, etc.; the bis(aminoalkyl) ethers, the n-alkyl bis (aminoalkyl) ethers, etc.; the polyoxyalkylene amines; the polyoxyalkylene polyamines, etc.; the alkoxyalkyl amines; amino-containing ethers derived from furan; and the like.

One preferred class of amino ethers is morpholine and the C-alkyl substituted morpholines. Another preferred class is the polyoxyalkyleneamines of molecular weight less than 1,000 and more preferably less than 500. Examples include the polyoxypropylenediamines of molecular weight less than about 400, and a polyoxypropylenetriamine of molecular weigt about 500. Both of the above types of compounds contain terminal primary amino groups.

The amount of a particular amine containing complexing agent utilized in forming the silver caroxylate/amine complex inpregnating solution is somewhat empirical. Generally that amount of amino complexing agent sufficient to completely dissolve the required amount of silver salt, which can be determined by observation. The amount of silver salt required is somewhat empirical and generally determined by the amount of silver ion required in solution and the porosity of the support.

As hereinbefore mentioned, it is desirable to have the complex as "rich" as possible in silver. Generally, the impregnating solution should contain an amount of about twice that desired in the finished catalyst on a wt. % basis with a support having about a 50% porosity. It is preferable, therefore, to obtain a complex which contains more than about 10 wt. % silver in the impregnating solution and more preferably from about 12 to about 25 wt. % silver.

When the preferred polyalkylene polyamines are utilized, it is desirable to have from about 1 to about 6 amine equivalents of silver in order to form the optimum complex containing solution.

The silver salt is preferably solubilized in the amine containing agent at temperatures in the range of about 20° C. to about 40° C. Temperatures in excess of 50° C. are not preferred, since higher temperatures tend to cause accelerated decomposition of the complex.

If desired, solubilizers can be added in order to facilitate dissolution of the silver salt in the amine complexing agent. Examples of such solubilizers include water, aqueous ammonia, and the like. In accordance with a preferred embodiment, water is utilized as the solubilizing agent. Water only reduces the viscosity of the impregnating solution, reduces the amount of amine required to solubilize the silver salt, and reduces potential hazards of handling the solution, but also acts as a solvent for the silver salt/amine complex, thus preventing premature precipitation.

Examples of suitable solubilizers include aqueous methylamine, ethylamine, diethylamine, triethylamine, and pyridine. It is, however, recognized that the marginal advantages of such solubilizers may be outweighed by the fact that certain lower molecular weight amines or ammonia can form explosive solids with silver. In addition, although not necessary, small amount of hydrogen peroxide or other suitable oxidizing agents may be added to minimize premature reduction of the silver in the complex.

The Support

The support utilized to form the novel silver catalyst of the instant invention can be generally described as a porous, inorganic substrate having those characteristics which are well known in the art and particularly known in the ethylene epoxidation art. Suitable supports which can be used in accordance with the instant invention are glass, alumina, silica, silica-alumina, inert metals, silicon carbide and zirconia. It is essential that the support chosen have a high porosity (i.e., high solvent absorption), low surface area and a controlled port size. Preferably, from about 70% to 100% of the pore diameters are between about 1 and 30$\mu$ and more preferably between about 1 and about 10$\mu$.

A preferred support media has an average pore diameter of from about 4 to about 6$\mu$0 with a pore volume of from about 0.3 to about 0.6 cc/g and has a surface area less than about 1 m$^2$/g. A particularly preferred support is high purity $\alpha$-alumina having the above characteristics.

Preparation of the Supported Silver Catalyst

In preparing the stable, supported silver catalyst of the instant invention, a suitable support is first contacted with the impregnating solution or mixtures thereof and subsequently heated at elevated temperatures to first evaporate the volatiles and finally to decompose the silver carboxylate/amine complex and activate the catalyst material. Although the preparation of the supported catalyst can be accomplished in two steps; i.e., an immersion step and an evaporation, activating, and decomposition step at incrementally increasingly elevated temperatures, it is preferable to prepare the catalyst of the instant invention in three distinct steps.

After the impregnating solution has been prepared, as described hereinabove, the substrate to be impregnated is contacted with the solution in a first step. This is preferably accomplished by immersion of the substrate in a suitably large body of impregnating solution to completely cover the substrate. The immersed substrate is then subjected to an evacuated atmosphere for a time period sufficient to remove entrapped air from the support pores at temperatures of from about 0° C. to about 50° C. and more preferably from about 20° C. to about 40° C.

The impregnation time will depend on the characteristics of the substrate and the viscosity of the impregnating solution and can be readily determined by the skilled artisan. Although somewhat empirical, it is generally sufficient to contact the porous substrate with the impregnating solution for a time from about five minutes to several hours. When utilizing impregnating solutions of silver salts of polyalkylene polyamines, a time from about ten minutes to two hours is sufficient. After the substrate has been contacted for sufficient time under vacuum, the vacuum is broken to return the pressure to atmosphere and then the excess solution is physically drained from the substrate.

In a second step the drained substrate is dried in the presence of heated flowing air, or a heated flowing inert atmosphere, at temperatures from about 50° C. to 150° C. for a period sufficient to evaporate the volatiles. Generally the time required to dry the impregnated substrate is somewhat empirical and can be readily determined by the skilled artisan for a particular substrate and impregnating solution. Time periods of from about one to about twelve hours have been found sufficent. It should be noted that during the drying step temperatures in excess of about 150° C. should be avoided as the complex may tend to decompose too rapidly and/or cause the volatiles to evaporate so readily as to disturb the uniformity of the catalyst material. Although not required, it is found that first thoroughly drying the impregnated substrate prior to thermal decomposition yields a more uniform catalyst.

In the third step the dried impregnated substrate is heated in the presence of flowing air, or a flowing inert atmosphere to temperatures in excess of about 180° C. and preferably from about 200° C. to about 300° C. to decompose the complexing agent and activate the supported silver catalyst materials. The time required to thoroughly decompose the silver salt/amine complex and activate the catalyst is somewhat empirical but generally times in the range from about one to about twelve hours have been found sufficient.

It will be realized by the skilled artisan that when other solubilizing agents such as water, aqueous ammonia, aqueous alkylamines, and the like are present in the complexing agent in accordance with the instant invention the times required for drying may be somewat variable depending on the solubilizing agents. The specific times required are generally within the above broad limits and can be determined by the skilled artisan without undue experimentation. Additionally, when higher molecular weight amines are utilized, washing of the dried substrate may be advantageous to remove excess organic material prior to activation. The washing may be accomplished in a conventional manner with lower alkanols or other suitable solvents.

The instant invention will be further illustrated by the following specific example, which are given by way of illustration and not as limitations on the scope of this invention.

EXAMPLE I

This example illustrates preparation of the stable supported silver catalyst employed in the instant invention. In a first step, silver oxalate was prepared. To an appropriate clean, dry vessel equipped with stirring apparatus were charged a solution of 18.4 g potassium oxalate dissolved in 150 cc of deionized water and a solution of 34.0 g silver nitrate in 150 cc deionized water. The two solutions were admixed at 60° C. and atmospheric pressure by stirring for several minutes. The mixture was then filtered and the residue washed with four aliquots of hot, deionized water totaling 50 cc. The residue was then further washed with two 25 cc aliquots of absolute methanol. The residue was then partially air dried by evacuating the lower portion of the filter surface.

In a second step, the dried silver oxalate and 30 ml of deionized water were added to a clean dry breaker and stirred until a slurry was obtained. To the stirred slurry was added 10 cc of $NH_4OH$ (30% $NH_3$ by weight) and 25 g of diethylenetriamine (DETA) yielding a dark, opague homogeneous solution having a mol ratio of Ag/DETA of about 0.65.

In a third step the solution prepared in step two was used as an impregnating solution. The impregnating solution was drawn into an evacuated clean dry 150 ml stainless steel sampling cylinder containing 75 g of a commercial pure alumina support (3/16" spherical pellets) having a pore volume of 0.41 cc/g, a surface area of less than about 1 $m^2/g$ and an average pore diameter of 5.9μ. The vacuum was maintained for about 10 to 15 minutes until the pressure had dropped to about 10 mm Hg. The vacuum was then released, and the container pressurized to 200 psig with nitrogen. After warming the cylinder to ambient temperature, the contents were allowed to stand under pressure for 30 minutes. The pressure was then released and excess solution drained.

In a fourth step the cylnder containing the wet impregnated material was attached to a forced-air heater, and heated to approximately 130° C. for 1 hour to dry the wet material. The dried material was then allowed to cool overnight.

In a fifth step the cylinder and contents were reheated to about 130° C., and then the temperature was raised to 250° C. over a period of about 1 hour and held at that temperature for an additional hour. After cooling, the recovered material weighed 85 g and had a silvery-tan appearance. Upon inspection, the interior of the supported catalyst appeared somewhat non-uniform and the material was again heated at 250° C. for an additional hour. After cooling, it was determined by analysis that the material contained 12.2 weight percent silver.

EXAMPLE II

This example illustrates the preparation of a supported catalyst employed in the process of the instant invention using a silver oxalate/diethylenetriamine impregnating solution. Silver oxalate was initially prepared, as described in the first step of Example I, added to 30 cc deionized water and stripped to form a slurry. To the slurry was added a mixture of 30 g diethylenetriamine and 10 cc deionized water, forming a dark, opague impregnating solution. The prepared impregnating solution was used to immerse 50 g of the pure α-alumina support material, as described in Example I (¼" spherical pellet). The support and covering solution was then placed under full pump vacuum. The vacuum was released to atmospheric pressure and the above sequence was once repeated. Upon draining, the wet impregnated support material was placed into a 150 cc sampling cylinder, which was attached to a forced-air heater, and dried at a temperature of about 120° C. for an hour. The sampling cylinder containing the dried material was then heated to about 250° C. over a 30-minute period and held at that temperature for an hour. After cooling, the recovered impregnated material weighed 56 g and had a silvery-gray appearance. Analysis showed presence of 11.0 weight percent silver.

EXAMPLE III

This example illustrates catalysts prepared for the process in the invention using an impregnating solution of silver oxalate and bis(2-aminoethyl)ether (BAEE). Silver oxalate was prepared as described in the first step of Example I and added to 50 cc deionized water containing 10 cc of $NH_4OH$ (30% $NH_3$ by weight) solution to form a stirred slurry. To the slurry was slowly added 25 g of distilled BAEE. An additional 10 cc of the $NH_4OH$ (30% $NH_3$ by weight) solution was added to dissolve the remaining undissolved materials. A dark homogeneous solution resulted.

Following the procedure in step 3 of Example I, the solution was drawn by suction into an evacuated 150 cc stainless steel sampling cylinder containing 75 g of the catalyst material described in Example I. The support was impregnated and dried substantially as described in Example I except that the drying temperature was 120° C. The dried catalyst was then treated in accordance with the procedure of step 5, Example I to produce 80 g of a uniform gray-tan material which, upon analysis, was shown to contain 7.7% by weight silver.

EXAMPLE IV

This example illustrates preparation of a catalyst employed in the invention using a silver oxalate/polyoxyalkyleneamine complex impregnating solution. As in Example I, the silver oxalate was prepared and added to 30 g deionized water to form a stirred slurry. To the slurry was added 60 g of a polyoxypropylenediamine (nw 230) sold under the tradename JEFFAMINE® D-230 by Jefferson Chemical Company, Inc. About 5 cc of aqueous $NH_4OH$ (30% $NH_3$ by weight) solution was added to solubilize the remaining trace amount of solids. The solution was drawn by suction into a cylinder which contained support material, as described in Example I. After impregnation, the remaining solution was drained. Drying was accomplished with forced air at a temperature of 120° C. for three hours. Prior to decomposition, the dried material was washed with anhydrous methanol for five hours in an extraction thimble to extract undecomposed organic matter. Although this washing step is not necessary, it may be utilized to facilitate removal of high molecular weight organic matter which may form a residue during the decomposition step at higher temperatures. In this example, the methanol wet catalyst was returned to the sampling cylinder and again dried at 120° C. for one hour prior to being heated at 250° C. for an additional hour to effect decomposition and activation. Upon cooling, the recovered material weighed 80 g, being slightly gray in color. Upon analysis, the material was shown to contain 9.0 weight percent silver.

EXAMPLE V

This example illustrates preparation of a catalyst used in the invention from silver oxalate and iminobis(propylamine) (IBPA) impregnating solution. Silver oxalate was prepared as described in Example I and added to a beaker containing 30 g of deionized water. After a homogeneous slurry was formed, 10 ml of concentrated NH4OH (30% NH3 by weight) was added; followed by 30 g of iminobis(propylamine). The solution was used, as in Example I, to impregnate 50 g of the 3/16" spherical alumina support of Example I. When the solution was drained, it was observed that crystallization of solids from the impregnating solution had occurred. The semi-solid was separated from the impregnated support using pressurized air. The contents of the cylinder were dried for about 17 hours with a forced-air heater at approximately 230° C. The dried material was then heated to about 250° C. over a period of one hour. The temperature was maintained for an additional hour. After cooling, the finished catalyst had a silvery-gray color and was observed to have a fairly heavy silver coating on the external surface. The catalyst, upon analysis was shown to contain 16.8 weight percent silver.

EXAMPLE VI

In this example, a prior art catalyst using silver oxalate, ethylenediamine and monoethanolamine was prepared in accordance with the procedure of Example I. Silver oxalate was prepared, as described in Example I, and added to a beaker containing 50 cc deionized water. To the resulting slurry was added a mixture of 14 g ethylenediamine (EDA) and 14 g monoethanolamine (MEA). The resulting solution was drawn by suction into an evacuated 150 cc stainless steel sampling cylinder containing 75 g of the 3/16" spherical support of Example I and the impregnation was carried out as therein described. The wet support was dried in a forced air heater at approximately 130° C. for two hours, and heated at approximately 250° C. for 3 hours in dry air. The material was a light tan color and contained 10 weight percent silver.

EXAMPLE VII

The six catalysts described above in Examples I-VI were tested for the process disclosed in a miniature ethylene oxide reactor, a 0.2 inch I.D. stainless steel tube, ten inches in length, operating at 200 psig and using 3.5 g of 30-40 mesh catalyst per test. The feed composition was approximately 7 mol % ethylene, 6 mol % oxygen, with the balance nitrogen and trace amounts of ethylene dichloride inhibitor. The reactor was operated at a temperature of 250° C. and mass velocity of about 5 g of feed per gram of catalyst per hour. Enough moderator was added to give maximum selectivity at the chosen ethylene oxide production rate. Selectivities and conversions are given in mol percent. Results are given in Table I.

TABLE I

| | Catalyst prepared according to indicated Examples | | | | | |
|---|---|---|---|---|---|---|
| | I (12.2)[1] | II (11.0)[1] | III (7.7)[1] | IV (9.0)[1] | V (16.8)[1] | VI[2] (10.0)[1] |
| Selectivity to ethylene oxide | 73 | 70 | 72 | 71 | 73 | 70 |
| C2H4 | 34 | 41 | 34 | 36 | 32 | 35 |
| Normalized selectivity at constant conversion of 32% | 73 | 72 | 72 | 72 | 73 | 70 |
| Reactor temperature | 250° C. | 250° C. | 250° C. | 250° C. | 230° C.[3] | 250° C. |

[1]Wt. % Ag by analysis [2]Prior art catalyst using solubilizing/reducing impregnating solution in accordance with the procedures of the instant invention
[3]A very high silver content made it impractical to operate this active catalyst at 250° C.

EXAMPLE VIII

Large scale preparation of catalyst for the invention using silver oxalate and DETA.

A large batch of fresh silver oxalate was prepared as follows: A 60° C. solution containing 102 g of silver nitrate, A.R., and 500 cc of deionized water was added slowly with stirring to an approximately 60° C. solution of 44 g of ammonium oxalate slurry, A.R., in 500 cc deionized water. The silver oxalate slurry was stirred for 20 minutes, then filtered through a Buchner funnel, washed with 300 cc deionized water and then with 300 cc anhydrous methanol in small portions. The silver oxalate was partially dried under aspirator vacuum of 10 mm mercury and added slowly to a beaker containing 100 cc deionized water to form an aqueous slurry. The slurry was chilled to below room temperature with an ice bath while a solution containing 90 g DETA and 30 ml deionized water was added slowly, keeping the solution temperature below 60° C. The silver solution was removed from the ice bath after all the DETA solution had been added and was stirred until all solids had dissolved.

The impregnating solution thus formed was added in sufficient quantity to cover the surface of 326 g of the 3/16" spherical alumina support (as described in Example I). The support and solution were placed under full pump vacuum, the vacuum released to atmospheric pressure and the immersed catalyst allowed to stand undisturbed for 30 minutes. The wet support was drained in a wire basket, then charged to a 500 cc stainless steel sampling cylinder which was attached to a forced-air heater. The impregnated support was dried at approximately 125° C. for one hour, then heated to 250° C. over a period of one hour, and maintained at 250° C. for one hour. After cooling, the catalyst was a uniform gray color inside and outside, weighed 259 g, and contained 9.7 weight percent silver.

The catalyst was tested in a pilot plant reactor operated at 245° C. with a total gas feed rate of about 896 liters/hour. As before, the feed consisted of 7% ethylene, 6% oxygen, but now contained 7.5 to 8% carbon dioxide, in addition to the other components.

Upon analysis, there was shown: conversion of ethylene, 25%; selectivity to ethylene oxide, 75% and ethylene oxide in effluent gas, 1.23 mol %. The productivity of the catalyst was 0.127 g ethylene oxide per gram of catalyst per hour.

A second test was then run using a prior art silver catalyst which is used in a commercial ethylene oxide process under substantially identical conditions. The commercial catalyst showed a maximum productivity of 0.0977. Thus, the catalyst of the instant invention shows an increase in productivity of about 20–25%.

EXAMPLE IX

The following example demonstrates the superior complexing characteristics of the amine containing complexing agents used in the instant invention. Four separate impregnating solutions were prepared substantially as in Example I, keeping the solution at a temperature below 50° C. Silver oxalate was used as the silver salt. The formed solutions and their respective characteristics are listed in Table II.

TABLE II

| | COMPLEXING AGENT | | | |
|---|---|---|---|---|
| | Morpholine (50 ml) | Piperidine (50 ml) | N-ethyl-morpholine (50 ml) | Tetrahydro-furfuryl amine (50 ml) |
| initial solubility of silver oxalate[1] | homogeneous, stable | silver plated from solution | slight or none, two phase[3] | homogeneous, stable |
| appearance on standing | trace of finely divided black precipitate | large amount of crystalline material | same as above, no change | Trace of finely divided precipitate |
| catalyst impregnation | no difficulty | N/A[2] | N/A[2] | No difficulty |

[1] Silver oxalate slurried in 30 ml water.
[2] No catalyst preparation - solution unsatisfactory for attempt.
[3] A second aliquot of 50 ml N-ethyl morpholine was added with no change.

While the invention has been explained in relation to its preferred embodiment, it is to be understood that various modifications thereof will become apparent to those skilled in the art upon reading the specification and is intended to cover such modifications as fall within the scope of the appended claims.

What is claimed is:

1. An improved method for epoxidizing ethylene to ethylene oxide in the vapor phase, which comprises the step of:
   intimately contacting ethylene with an epoxidizing amount of a molecular oxygen epoxidizing agent in the presence of a supported silver catalyst at epoxidizing temperatures from about 200° C. to about 300° C.,
   wherein the catalyst is prepared by;
   contacting a porous, inorganic catalyst support material with an impregnating solution comprising a silver carboxylate/amine complex; and,
   heating the impregnated support material at temperatures from about 50° C. to 300° C. to evaporate volatiles, decompose said complex and activate said catalyst,
   wherein said silver carboxylate/amine complex comprises a silver carboxylate dissolved in a solubilizing amount of an amine containing complexing agent and wherein the said complexing agent is tetrahydrofurfurylamine.

2. The method of claim 1 wherein the said ethylene is contacted with a molecular oxygen epoxidizing agent in the presence of the said supported silver catalyst and in the presence of an effective amount of at least one inhibitor to retard the combustion of ethylene to carbon dioxide.

3. The method of claim 1 wherein the said ethylene is contacted with a molecular oxygen epoxidizing agent in the presence of said supported silver catalyst and in the presence of an effective amount of ethylene dichloride to retard combustion of ethylene to carbon dioxide.

4. The method of claim 1 wherein the said inpregnating solution further contains a substantial amount of water.

5. The method of claim 1 wherein the said silver carboxylate is selected from the group consisting of silver salts of monocarboxylic acids, dicarboxylic acids and mixtures thereof wherein the organic moiety contains less than about 10 carbon atoms.

6. The method of claim 1 wherein said silver carboxylate is selected from a group consisting of silver carbonate, silver acetate, silver malonate, silver glycolate, silver oxalate, silver formate, silver citrate, silver lactate and silver pyruvate.

7. The method of claim 1 wherein said support material is a high purity α-alumina material having an average pore diameter of from about 4 to about 6μ with a pore volume of from about 0.3 to about 0.6 cc/g and a surface area less than about 1 m²/g.

8. The method of claim 1 wherein the epoxidizing temperature is between about 220° C. and 260° C., and a pressure of from about 13 atmospheres to 20 atmospheres.

* * * * *